United States Patent [19]

Silbergeld

[11] Patent Number: 5,354,652
[45] Date of Patent: Oct. 11, 1994

[54] LEAD ASSAY

[75] Inventor: Ellen K. Silbergeld, Baltimore, Md.

[73] Assignee: The University of Maryland at Baltimore, Baltimore, Md.

[21] Appl. No.: 55,761

[22] Filed: May 3, 1993

Related U.S. Application Data

[63] Continuation of Ser. No. 728,484, Jul. 11, 1991, abandoned.

[51] Int. Cl.$^5$ .......................... C12Q 1/00; C12Q 1/32; C12N 11/00; G01N 33/20
[52] U.S. Cl. .......................... 435/4; 435/26; 435/174; 435/176; 436/77; 436/178; 436/74
[58] Field of Search .................. 435/4, 25, 26, 176, 435/174; 436/80, 77, 178, 74, 177

[56] References Cited

U.S. PATENT DOCUMENTS 5,010,020  4/1991  Gould .................................. 436/77
5,039,618  8/1991  Stone .................................. 436/77

FOREIGN PATENT DOCUMENTS 0286039  10/1988  European Pat. Off. .
3146864  6/1991  Japan .

OTHER PUBLICATIONS

Chiba et al; Chemical Abstracts, vol. 87(23):179588u.
Cifarelli et al; Chemical Abstracts, vol. 81(5):21895h.
Nikkanen et al; Chemical Abstracts, vol. 77(25):16078h.
Witting et al; Chemical Abstracts, vol. 107(5):34432k.
Teramoto et al; Chemical Abstracts, vol. 84(15):101269j.
Fukano et al; Chemical Abstracts, vol. 109(26):236123n.
Reagan et al, *Trace Substance Environmental Health*, 23:199–283 (1989).
Silbergeld, *Environmental Health Perspectives*, 89:49–54 (1990).
Porter, *Laboratory Information Bulletin*, No. 152, Jan. 8, 1973.
Takebayashi et al, "Evaluation of δ-aminolaevulinic acid in blood of workers exposed to lead", *British J. of Industrial Med.*, 50:49–54 (1993).
Chisolm et al, "Erythrocyte Porphobilinogen Synthase Activity as an Indicator of Lead Exposure in Children", *Clinical Chemistry*, 31:601–605 (1985).
Silbergeld et al, "Neurotoxic Aspects of Porphyrinopathies: Lead and Succinylacetone", *Environmental Res.*, 29:459–471 (1982).
Silbergeld, "Role of Altered Heme Synthesis in Chemical Injury to the Nervous System", *Annals New York Academy of Sciences*, 297–308.
Silbergeld et al, "Effects of Altered Porphyrin Synthesis on Brain Neurochemistry", *Neurobehavioral Toxicology and Teratology*, 4:635–642 (1982).
Centers for Disease Control: *Preventing Lead Poisoning in Young Children*, Oct. 1991.
Kondo et al, *Clinical Chemistry*, 3:427–429 (1985).
Tomokuni, *Clinical Chemistry USA*, 20/10:1287–1291 (1974).
Comoy et al, *Clinical Chim. ACTA (Netherlands)*, 147/2:179–181 (1985).
Astrin et al, *Ann. N.Y. Acad. Sci.*, 514:23–29 (1987).
Jordan et al, *Methods in Enzymology*, 123:427–434 (1986).
Jaffe et al, *Biological Trace Element Research*, 28:223 (1991).

*Primary Examiner*—Michael G. Wityshyn
*Assistant Examiner*—Louise N. Leary
*Attorney, Agent, or Firm*—Sughrue, Mion, Zinn, Macpeak & Seas

[57] ABSTRACT

Lead assays using δ aminolevulinic acid dehydratase are disclosed.

7 Claims, No Drawings

LEAD ASSAY

This is a continuation of application Ser. No. 07/728,484, filed Jul. 11, 1991 now abandoned.

FIELD OF THE INVENTION

The invention relates to assays for lead. The assays are rapid and sensitive with medical and environmental applications.

BACKGROUND OF THE INVENTION

The rapid and accurate measurement of lead in biologic, environmental and product materials is of major importance in public health and ultimately in the prevention of lead poisoning. Lead poisoning is caused solely by exposure to and absorption of the heavy metal. Lead may exist in various compound forms, such as oxides, halides, carbonates and acetates. Because it is lead itself that is toxic, the chemical and physical form of lead only slightly influences toxicity by modulating absorption and retention.

Lead poisoning is treatable poorly for two reasons: first, it is difficult to remove lead from critical target organs once it is absorbed; and second, some of the target organ damage induced by lead appear to be irreversible.

Prevention of lead poisoning requires two strategies to succeed: early detection of increased absorption and identification of lead in sources. Early detection is based on biological monitoring. Source identification is based on sampling air, drinking water, dusts, soils and food. For many children in the U.S., a major source of lead in dusts and soils is from old paint thereby making the measurement of lead in painted surfaces another priority. Also, for some environmental applications, measuring lead in soils, sediments and wastes is an important requirement.

Screening persons suspected to have been exposed to lead is based on two principles: measuring lead in blood, urine, bone, teeth or hair; and measuring biological markers or early cellular responses to lead. Direct measurement of lead requires collecting appropriate samples, extracting lead from the biological matrix and analyzing using atomic absorption spectrophotometry (AAS). The analytic phase requires laboratory support, investment in and maintenance of fixed laboratory equipment, skilled technical operators and inevitably delay between sampling people and obtaining an analytical result. For example see Pruszkowska et al. (1983) *Atomic Spec.* 4, pp. 59–61; and Barthel et al. (1973) *J. A.O.A.C.* V.56, No. 5.

Lead can also be measured in aqueous media, such as water and extracted blood, by electrochemical methods using a lead-specific electrode. The method is known as anodic stripping voltametry and (ASV) relies on the principle of measuring conductance changes associated with the plating and discharge of lead ions in solution. A portable ASV device is available, however, the method is limited in sensitivity.

An alternative method of screening for possible lead exposure was developed in the 1950's and is based on the effects of lead on cellular heme synthesis (in general, see papers in Silbergeld, EK & Fowler, BA (eds.) *Mechanisms of Chemical-Induced Porphyrinopathies*, Ann. NY Acad. Sci. (1987) v. 514). Lead is known to alter heme synthesis, common to many cells, at several steps. Because the pathway is under considerable internal feedback control, substantial alterations in the amounts of final product (heme) and various intermediates can be measured. Thus, measurement of aminolevulinic acid (ALA), coproporphyrins and protoporphyrin have been utilized as markers for lead poisoning. Also, activity of the rate-limiting enzyme, ALA dehydrase (ALAD), has been measured (see Doss; Marks et al.; Bernard & Lauwerys in Silbergeld and Fowler, supra).

In the early 1970's, Piomelli and coworkers demonstrated that measuring protoporphyrin in red cells was an accessible and reliable marker for lead exposure in children. Since that time, measuring protoporphyrin (frequently called erythrocyte protoporphyrin (EP) or "free" erythrocyte protoporphyrin (FEP)) is the standard method for screening children and adults for lead exposure. The EP assay requires small samples of blood collected by fingerstick and a portable instrument (the hematofluorometer) was built to provide an instant readout for purposes of clinic-based screening. Throughout the 1970's and 1980's, EP screening was the method of choice in public health to detect both childhood and occupational lead exposure.

However, it was known from the 1970's that there were significant limits to the utility of EP as a screening tool. For example, EP is influenced by iron status of individuals and EP does not rise significantly until blood lead levels are above 30 $\mu$g/dl. (Micrograms per deciliter is the standard designation for blood lead concentrations; some authorities recommend using the international unit of micromolar, $\mu$M; roughly, 20 $\mu$g/dl equals 1 $\mu$M.) Thus there are limits of both specificity and sensitivity with the EP assay.

Measuring lead in sources requires the appropriate sampling techniques, extraction of lead from environmental media or product matrices and analysis of lead by AAS. Before the development of AAS, lead was measured in a chemical reaction utilizing dithizone and formation of a lead-sulfide complex (see Chisolm et al. (1955) *Amer. J. Disease of Children* 89, pp. 159–168). Although the method has been replaced almost completely by AAS, a recent home test kit based on the dithizone reaction has been marketed for measuring lead leached from ceramics and cans (Frandon Enterprises). However, the test kit is considered by some to be unreliable.

Lead also can be analyzed by ion-coupled inductive plasma techniques and by x-ray induced fluorescence spectrophotometry. The former method is primarily a research tool and is used in studies, for example, of specific ion monitoring to determine sources of environmental contamination or of human exposure. The latter method has been adapted for use with portable equipment specifically detecting lead in painted surfaces such as interior woodwork. The sensitivity and reliability are less than ideal and furthermore, the equipment requires a radioactive source to generate x-rays.

Clearly current methods of lead assay are far from ideal. The shortcomings become amplified in view of recent developments in knowledge and public policy regarding lead that demand advances in screening and source identification. With respect to screening, it is generally recognized that lead toxicity occurs in children at blood lead levels as low as 10–15 $\mu$g/dl. Although occupational health policy has not been updated since 1977 (the publication of the OSHA lead standard), recent data strongly indicates that an appropriate standard for preventing occupational lead poisoning is considerably lower than the current blood lead level of 40

μg/dl (see Silbergeld et al. (1991), *New Solutions*, in press).

Recent surveys indicate that lead poisoning, defined as exposures resulting in blood lead levels in excess of 10–15 μg/dl in children, is very prevalent in the U.S. (Agency for Toxic Substances and Disease Registry (ATSDR), *Report to Congress on the Nature and Extent of Childhood Lead Poisoning*, 1988). The problem has causes in the many widespread sources of lead in the environment, including the food supply. As a consequence, the Centers for Disease Control have recommended that all children be screened for lead exposure starting at 6 months of age and continuing at least yearly thereafter until age 6 (U.S. Public Health Service, *Strategic Plan for the Elimination of Childhood Lead Poisoning*, February 1991). Furthermore, increased surveillance of workers is clearly required to prevent occupational disease (Silbergeld et al., 1991, supra). Soon it is likely there will be recommendations to assess lead exposure in pregnant women and in the elderly based upon new epidemiologic studies on the effects of lead in those populations (Silbergeld, *Environmental Health Perspectives* 91: 156, 1990).

With respect to source identification, the recognition that lead at low doses is toxic necessarily results in the need to detect levels of lead in environmental and dietary sources at lower levels, and in the need to develop proactive programs of environmental monitoring of media such as dust and soils. As an example, the EPA has lowered the drinking water standard to an advisory level of 5 parts per billion (ppb), one-third of the current standard, and lowered the air standard from 1.5 μg/cubic meter to 0.5 mg/cubic meter. Current federal and state guidelines for cleaning up contaminated dusts and soils range between 100 and 750 ppm (Reagan & Silbergeld, Trace Substances in Environmental Health in Environmental Geochemistry & Health (1990) 12, Suppl., 199–238). The FDA is proposing a lowered level for allowance leaching of lead from ceramic vessels.

At present there are no acceptable methods for identifying lead in humans or sources without laboratory based analytic support, almost always AAS, a resource intensive process. More significantly, for purposes of early detection and prevention, the need to send samples to a laboratory introduces substantial delays between sample collection and results. In screening programs the delay can be 1–3 months making it difficult to develop timely intervention and to implement treatment programs. Universal screening of all children is likely to be recommended. The impact on state and local screening programs will be enormous. Less than 5% of all children under 6 years currently are screened and almost all of the screening is done with EP as the first tier. The CDC have no recommendations as to alternate methods aside from venous blood and AAS and thus development of a new screening method is one of the highest priorities for eliminating lead poisoning (Public Health Service, 1991, *Strategic Plan for Elimination of Childhood Lead Poisoning*).

The criteria for a screening and detection method for lead exposure and of lead sources are those that relate to all such methods. First, the methods must be reliable and specific, that is, measure lead and not other metals, ions, or substances. The assays should not be confounded by commonly occurring conditions. Second, the assays must be appropriately sensitive, that is, generate a signal that detects lead or lead exposures at levels of current concern (for instance, in blood, concentrations of lead as low as 2–5 μg/dl; concentrations in water as low as 1 ppb ) .

Additional criteria for screening and detection methods to be useful in public health include: the methods should produce results within the constraints of clinic and outpatient screening, that is, should utilize small amounts of sample (for instance, a fingerstick sample of blood or a single urine collection); should provide answers quickly within the clinic setting; should be relatively inexpensive; should be stable within a range of environmental settings, such as temperature; should be usable by persons with minimal technical training; and should be portable.

SUMMARY OF THE INVENTION

An object of the invention is to provide rapid and sensitive lead assays suitable for clinic, public health, screening, environmental, other medical and other industrial applications.

DETAILED DESCRIPTION OF THE INVENTION

The above-noted and other objects have been achieved in the development of new assays for lead assessing δ aminolevulinic acid dehydrase (ALAD) activity or presence of the ALAD-Pb complex.

The action of lead on heme biosynthesis has been known for several decades. EP, ALA and ALAD have all been used as biological markers for lead exposure. EP has been used most frequently because of the development of relatively easy and inexpensive measurement technology, although urinary ALA also has been used for screening, particularly in occupational medicine in Europe. It should be noted that assay of all heme markers has to be followed up with direct measurement of lead in blood or urine to confirm exposure. Direct confirmation is unnecessary in the instant invention.

In the heme system of mammals, ALAD is one of the enzymes most sensitive to lead. Lead inhibits red cell ALAD at blood lead concentrations of about 5 μg/dl (Hernberg, *Pracov. Lek.* (1972) 24, 77–83). However, as will be appreciated in the discussion to follow, it was noted that in vitro, exposure of lead to purified enzyme produces measurable inhibition at concentrations of about one-tenth that level thereby affording the development of the instant assays of enhanced sensitivity. Although it is not completely known how lead inhibits ALAD, it is thought that lead may displace zinc from its binding site and consequently alter the conformation of the protein, thus lowering or destroying the catalytic activity of ALAD.

Measurement of enzyme activity is done classically by measuring production of porphobilinogen (PBG) from ALA under specified conditions. Generally, the reaction is monitored by spectrophotofluorometry.

While ALAD activity in red cells has in the past been utilized as a marker for lead exposure, the principle of the instant invention is to use ALAD as a biodetector instead of a biomarker. The assays employing ALAD as a biodetector have a sensitivity of at least 0.5 μg/dl, or 5 ppb, lead.

Several strategies for developing an enzyme-based biodetection system for lead using ALAD can be considered.

Samples can be obtained from a variety of sources, including physiologic fluids, such as blood and urine; organ, tissue and cell lysates or homogenates; dried paint files; leachates; water and other aquatic samples; sludge or wastes; dust, sediment or soil samples; animals; research samples and the like.

Essentially any matrix suspected of containing lead can be analyzed so long as the lead is liberated from the matrix in which it is presented to produce elemental lead. A common method for liberating lead from a matrix is nitric acid extraction. Lead-free reagents and materials are used. For example, all glassware is acid-washed prior to use. A suitable procedure is treating glassware with nitric acid (about 30% v/v) for about twenty-four hours followed by profuse rinsing with lead-free deionized water. The glassware is then oven-dried. Sterile disposable supplies known to be lead-free can be used also.

The nitric acid treatment can be conducted under elevated temperature conditions. For example, a dust sample is suspended in 7M nitric acid and heated at 120° C. for two hours or a paint film sample is placed in concentrated nitric acid and gently boiled for three hours. The sample can be neutralized with a physiologic buffer, such as with a sodium acetate solution.

ALAD can be obtained from tissues using procedures taught in the art. For example, liver supernatant is a suitable source of ALAD. Alternatively, ALAD has been purified to homogeneity from many species, including humans, and may be purchased commercially, for example, from Sigma, St. Louis, Mo.

Polyclonal and monoclonal antibodies to ALAD can be made with the purified antigen using methods known in the art. Thus, suitable animals, such as rabbit, sheep and goat are immunized repeatedly with ALAD, with or without adjuvent as determined by the artisan, and the sera obtained. Specificity and titer can be determined in any of a variety of immunoassays using ALAD and suitable reporter molecules.

Alternatively, animals suitable for making monoclonal antibodies, such as the mouse, are immunized and immune cells, such as splenocytes are obtained from the immune animal. The immune cells are fused with suitable myeloma cells and the heterokaryons cultured. Those clones secreting specific antibody, determined as described above, are isolated and either propagated in vitro or in vivo to obtain quantities of ALAD antibody.

The invention contemplates at least two different modes of using ALAD as a biodetector for lead, the first measuring the activity of ALAD after exposure to samples suspected of containing lead and the second measuring the amount of ALAD complexed to lead.

As to measuring enzyme activity, that can be achieved, for example by monitoring the amount of product formed or the amount of substrate utilized. Either approach can be achieved, for example, by conjugating or attaching a label, such as a chromophore, to either the substrate or product and quantifying the amount of labeled material present after a defined reaction period.

Labelled compounds are produced using art-recognized techniques and reagents. For example, ALA can be made to contain a substituent that upon cleavage from ALA in the process of making porphobilinogen either the cleaved substituent is detectable, for example, spectrophotometrically or the ALA-substituent complex loses a detectable characteristic following cleavage. In a similar vein, the reaction mixture can contain a compound that upon binding to porphobilinogen offers a detectable signal or a loss of signal.

Porphobilinogen, the natural product of ALAD in situ, is fluorescent, enabling fluorescence monitoring of the reaction mix to be a suitable means of monitoring enzyme activity, provided the appropriate measures are maintained (porphobilinogen is photosensitive).

Alternatively, the amount of substrate utilized or product made can be determined indirectly, by for example, an antibody which binds specifically to substrate or to product. Thus, a relevant antibody is added to the reaction mix following a reaction period and a suitable assay such as an ELISA, sandwich assay, agglutination assay, RIA and the like can be used to monitor the extent or completeness of the ALAD reaction.

Another approach which does not require monitoring enzyme activity is to determine whether lead is bound to ALAD. That can be done, for example by using an antibody that binds specifically to the unoccupied lead binding site of ALAD, to the occupied binding site of ALAD or to binding sites that appear or disappear as a result of ALAD binding lead, for example.

The antibodies for determining enzyme activity or the ALAD-lead complex can be obtained using art-recognized techniques. All of the antigens, substrate, product, ALAD and the ALAD-lead complex, are available and are used in a suitable fashion to assure an adequate immune response in a selected host, for example mouse, horse, sheep, rabbit or goat. Specificity of the antibodies is tested using art-recognized immunologic methods, such as ELISA, complement dependent cytotoxicity and RIA. Polyclonal sera can be made monospecific by absorption to minimize non-specificity.

Additionally, monoclonal antibodies can be produced. Suitable hosts, for example mouse, are immunized and appropriate myeloma partners, such as NS-1 and Sp2/0, are fused with immune spleen cells to produce heterokaryons. The heterokaryons are propagated using known selection procedures, such as using HAT, and cloned. Clones are screened by ELISA, for example, using the cognate antigen bound to the solid phase.

The assay reagents can be provided conveniently in the form of kits. Thus, for example, a first vessel comprises a diluent; a second vessel comprises substrate; a third vessel comprises ALAD; a fourth vessel comprises lead extracting solution; and a fifth vessel comprises a buffer. The reagents can be in the form of a liquid or a lyophilized powder for reconstituion with a suitable liquid carrier, such as deionized water. For an antibody-based assay, of which many such kits are available in the art, 96-well plates or other solid phase such as a dipstick with bound antibody is provided in a kit. The appropriate buffers and reagents for conducting the assay, for example ELISA with color producing substrate, are included. Alternatively, antibody can be provided in a vessel for an agglutination reaction, with the appropriate reagents included in separate vessels.

Certain aspects of the invention are disclosed in greater detail in the following non-limiting examples.

EXAMPLE 1

To extract lead from a dried paint film, the following procedure can be practiced. An aluminum block is placed on a hot plate and allowed to heat. The temperature is adjusted to 160°–170° C. If an aluminum block is unavailable, a sand bath can be used. Weigh to 0.1 mg, enough paint in a tared test tube to provide 4 mg of lead but not more than 0.5 g of the dried paint film.

If the paint is liquid, it is spread as a film on a glass plate and oven dried at 100°–105° C. for three hours (wet film thickness max. -0.006inch). The dried paint film is removed from the glass with a clean, single edge razor blade.

If the paint is a film on a toy, the paint should be removed as completely as possible from the substrate by scraping or by softening with a small amount of methylene chloride. It is important that the paint film be removed as completely as possible from the substrate since in some instances the pigment is not uniformly distributed throughout the film. With metal toys the problem is generally not as severe as with wooden or composition based toys. As little of the substrate as possible should be included in the paint sample. The methylene chloride is removed from the paint film by heating in a 60° C. oven for 15 minutes. The dried paint film is weighed into a tared 16×150 mm test tube (0.05 to 0.5 g).

Pipet into each sample containing test tube and into two blanks, 5 ml of concentrated nitric acid and add two small boiling stones. The samples and blanks are placed in the aluminum block and gently boiled for three hours. The test tubes are allowed to cool and the contents transferred to a 25 ml volumetric flask. The test tubes are rinsed with 4×4 ml of water and the flasks brought to volume with water. The precipitate present in most paints is allowed to settle for ½ hour.

EXAMPLE 2

To ascertain blood lead levels, the following procedure can be followed. Aspirate a 10 µl blood sample and dispense the sample and 50 µl of 0.5% $HNO_3$ diluent into a tube. Then, aspirate 10 µl of lead-free $H_2O$ and 50 µl of 0.5% $HNO_3$ into the tube. An additional 50 µl of 0.5% $HNO_3$ is added to the tube yielding a total volume of 170 µl. The diluted samples are evaporated to dryness in an oven at 180°–200° C. for one hour and reconstituted with lead-free distilled water.

EXAMPLE 3

An alternative method of obtaining lead from a blood sample is as follows. Aspirate a 30 µl blood sample and dispense the sample and 90 µl of 0.5% Triton X-100 diluent into a small glass tube. Dispense an additional 180 µl of 0.5% Triton X-100 into the same tube to obtain a 1:10 dilution. Mix the tube contents by swirling gently (Vortex, low setting).

EXAMPLE 4

To prepare dust samples for acid digestion, the following procedure can be followed. All glassware must be acid washed prior to use. Soak glassware in 30% v/v nitric acid/deionized water and rinse with deionized water. Oven dry the glassware and cool to room temperature. Tare a 100 ml beaker and transfer a dust sample to the beaker. Weigh to obtain the sample weight.

To the sample add 25 ml of 7M nitric acid, washing down any dust attached to the inside walls of the beaker. Cover each sample with a watchglass and heat at 120° C. for two hours in a fume hood. Cool beakers.

Transfer samples to 25 ml or 50 ml volumetric flask, depending on the weight of the sample. Rinse beaker with small amount of 1M nitric acid and add to flask. Repeat rinses to bring volume to that of the flask. Mix well and filter the samples through Whatman*#42 filter paper (or equivalent) using polypropylene funnels into new Falcon test tubes.

EXAMPLE 5

Substrate was prepared by mixing 0.0061 g glutathione and 0.0036 g ALA in 4.0 ml of 5M sodium acetate (all reagents are available commercially). One-half milliliter of substrate solution was added to a flask and varying concentrations of lead acetate were mixed with the solution. The mixture was allowed to incubate for 10 minutes at room temperature. Then 0.25 ml liver supernatant (the 100,000×g supernatant of a liver homogenate) was added to the flask and the contents were incubated for an additional 60 minutes at room temperature. The reaction was stopped by adding 0.5 ml of 10% trichloroacetic acid prepared in 0.1M HgCl.

The reaction mixture was centrifuged (9500 rpm for 10 minutes in glass test tubes; centrifugation not necessary if pure ALAD is used) and the supernatant decanted. Then 0.25 ml of Ehrlich's reagent (comprises p-dimethylaminobenzaldehyde, available from Sigma) were added to each tube, the tube contents were incubated for 10 minutes at room temperature and scanned spectrophotometrically. A 1:1 by volume ratio of Ehrlich's reagent to water served as a blank (1.5 ml total volume).

When ALAD activity was plotted against lead concentration, a clear dose-response was observed in the 0–100 ng range of lead. The routine sensitivity of the assay with lead standards is 10 ng lead which is equivalent to 1 µg/dl of blood.

EXAMPLE 6

Antibody to ALAD complexed with lead can be obtained by using the ALAD-Pb complex as antigen in a suitable host, such as mouse, horse, sheep, rabbit and goat. A polyclonal antibody can be absorbed with ALAD alone and lead alone to obtain an antibody specific for the complex. Alternatively, the ALAD-Pb complex can be affixed to a solid matrix to produce an affinity column and the polyclonal antisera can be passed over the column and the ALAD-Pb-specfic antibody eluted.

Alternatively, a monoclonal antibody to the ALAD-Pb complex can be made using the same screening strategy to validate specificity as described above.

A suitable assay is as follows. The ALAD-Pb-specific antibody (monospecific polyclonal or monoclonal) is affixed to the wells of a 96-well microtiter plate such as by drying or with glutaraldehyde. The plates are used immediately or can be stored. A sample suspected of containing elemental lead is mixed with ALAD. Following a suitable reaction time, a portion of the mixture is added to wells of the antibody-coated microtiter plate. Following an incubation, the wells are washed and exposed to an enzyme-labelled ALAD antibody, either purchased commercially or produced as described above. A suitable label is horseradish peroxidase. Following incubation, the wells are washed and a substrate, such as o-phenylenediamine/$H_2O_2$, is added to the wells. The amount of labelled ALAD antibody present, and thus the amount of ALAD-Pb bound to the plate and the amount of lead in the sample, is determined, for example spectrophotometrically at 492 nm in the example above.

It will be appreciated that the instant specification and claims are set forth by way of illustration and are not to be considered as limiting. The artisan will realize that various modifications and changes can be made to the teachings contained herein without departing from the spirit and scope of the invention.

I claim:

1. A quantitative method for determining the amount of lead in a sample comprising the steps of:
   (a) obtaining a lead containing sample, solubilizing the lead in said sample and inactivating any endogenous δ aminolevulinic acid dehydratase which may be present in said sample;
   (b) adding the resulting solubilized lead sample, or an aliquot thereof, to a buffered solution comprising:
      (i) substantially pure exogenous δ aminolevulinic acid dehydratase, or
      (ii) a substrate for said dehydratase, so as to form an admixture;
   (c) adding the other of said substantially pure exogenous δ aminolevulinic acid dehydratase or said substrate to said admixture of step (b); and
   (d) measuring the amount of product resulting from reaction of said dehydratase and said substrate, wherein the amount of lead in said sample, or an aliquot thereof, is inversely and stoichiometrically related to the amount of product formed.

2. The method as claimed in claim 1, wherein in step (a) said lead is solubilized with nitric acid or a detergent.

3. The method as claimed in claim 1, wherein said sample is selected from the group consisting of blood, urine, paint, dust, water, soil, sludge and sediment.

4. The method as claimed in claim 3, wherein said sample is blood.

5. The method as claimed in claim 1, wherein said sample is added to a buffer comprising exogenous δ aminolevulinic acid dehydratase.

6. The method as claimed in claim 1, wherein said sample is added to a buffer comprising δ aminolevulinic acid dehydratase substrate.

7. The method as claimed in claim 6, wherein said substrate is labelled δ aminolevulinic acid.

* * * * *